United States Patent
Fonsny et al.

[11] Patent Number: 5,948,743
[45] Date of Patent: Sep. 7, 1999

US005948743A

[54] SPRAYABLE CLEANING COMPOSITION COMPRISING ACARICIDAL AGENT

[75] Inventors: Pierre Fonsny, Fays; Marianne Mahieu, Ferrieres; Germaine Zocchi, Villers-Aux-Tours, all of Belgium; Betty Kong, Westfield, N.J.

[73] Assignee: Colgate Palmolive Company, NY, N.Y.

[21] Appl. No.: 09/109,794

[22] Filed: Jul. 2, 1998

Related U.S. Application Data

[63] Continuation-in-part of application No. 08/938,637, Sep. 26, 1997, abandoned, which is a continuation-in-part of application No. 08/801,725, Feb. 10, 1997, abandoned, which is a continuation-in-part of application No. 08/671,470, Jun. 28, 1996, Pat. No. 5,719,114.

[51] Int. Cl.$^6$ .............................. C11D 3/48; C11D 3/50; C11D 3/60

[52] U.S. Cl. ..................... 510/280; 510/101; 510/102; 510/103; 510/104; 510/279; 510/319; 510/342; 510/350; 510/356; 510/406; 510/421; 510/423; 510/433

[58] Field of Search ................ 510/383, 278–280, 510/319, 342, 356, 360, 406, 421, 426, 432, 102, 103, 104, 106, 107, 506, 423, 433, 350

[56] References Cited

U.S. PATENT DOCUMENTS

| | | | |
|---|---|---|---|
| 4,977,142 | 12/1990 | Green | 514/23 |
| 5,178,871 | 1/1993 | Thill | 424/405 |
| 5,288,483 | 2/1994 | Cardin et al. | 424/70 |
| 5,292,504 | 3/1994 | Cardin et al. | 424/70 |
| 5,569,411 | 10/1996 | Steltenkamp et al. | 510/383 |
| 5,573,700 | 11/1996 | Steltenkamp et al. | 510/383 |
| 5,612,047 | 3/1997 | Duffy et al. | 424/405 |
| 5,719,114 | 2/1998 | Zocchi et al. | 510/383 |

*Primary Examiner*—Ardith Hertzog
*Attorney, Agent, or Firm*—Richard Nanfeldt

[57] ABSTRACT

The present invention relates to a sprayable composition for the treatment of soft surfaces and containing 0.05 to 5.0 wt. % of an acaricidal agent.

3 Claims, No Drawings

SPRAYABLE CLEANING COMPOSITION COMPRISING ACARICIDAL AGENT

RELATED APPLICATIONS

This application is a continuation in part application of U.S. Ser. No. 8/938,637 filed Sep. 26, 1997 now abandoned which in turn is a continuation in part application of U.S. Ser. No. 8/801,725 filed Feb. 10, 1997 now abandoned which in turn is a continuation in part application of U.S. Ser. No. 8/671,470 filed Jun. 28, 1996 now U.S. Pat. No. 5,719,114.

FIELD OF THE INVENTION

This invention relates to an improved sprayable composition, preferably but not limited to a microemulsion form, containing an acaricidal agent and designed in particular for treating soft surfaces such as mattresses and upholstery and which is effective in killing dust mites.

BACKGROUND OF THE INVENTION

In recent years all-purpose liquid detergents have become widely accepted for cleaning hard surfaces, e.g., painted woodwork and panels, tiled walls, wash bowls, bathtubs, linoleum or tile floors, washable wall paper, etc. Such all-purpose liquids comprise clear and opaque aqueous mixtures of water-soluble synthetic organic detergents and water-soluble detergent builder salts. In order to achieve comparable cleaning efficiency with granular or powdered all-purpose cleaning compositions, use of water-soluble inorganic phosphate builder salts was favored in the prior art all-purpose liquids. For example, such early phosphate-containing compositions are described in U.S. Pat. Nos. 2,560,839; 3,234,138; 3,350,319; and British Patent No.1, 223,739.

Another approach to formulating hard surfaced or all-purpose liquid detergent composition where product homogeneity and clarity are important considerations involves the formation of oil-in-water (o/w) microemulsions which contain one or more surface-active detergent compounds, a water-immiscible solvent (typically a hydrocarbon solvent), water and a "cosurfactant" compound which provides product stability. By definition, an o/w microemulsion is a spontaneously forming colloidal dispersion of "oil" phase particles having a particle size in the range of 25 Å to 800 Å in a continuous aqueous phase.

In view of the extremely fine particle size of the dispersed oil phase particles, microemulsions are transparent to light and are clear and usually highly stable against phase separation.

Patent disclosures relating to use of grease-removal solvents in o/w microemulsions include, for example, European Patent Applications EP 0137615 and EP 0137616—Herbots et al; European Patent Application EP 0160762—Johnston et al; and U.S. Pat. No. 4,561,991—Herbots et al. Each of these patent disclosures also teaches using at least 5% by weight of grease-removal solvent.

However, since the amount of water immiscible and sparingly soluble components which can be present in an o/w microemulsion, with low total active ingredients without impairing the stability of the microemulsion is rather limited (for example, up to 18% by weight of the aqueous phase), the presence of such high quantities of grease-removal solvent tend to reduce the total amount of greasy or oily soils which can be taken up by and into the microemulsion without causing phase separation.

The following representative prior art patents also relate to liquid detergent cleaning compositions in the form of o/w microemulsions: U.S. Pat. Nos. 4,472,291—Rosario; 4,540, 448—Gauteer et al; 3,723,330—Sheflin; etc.

Liquid detergent compositions which include terpenes, such as d-limonene, or other grease-removal solvent, although not disclosed to be in the form of o/w microemulsions, are the subject matter of the following representative patent documents: European Patent Application 0080749; British Patent Specification 1,603,047; U.S. Pat. Nos. 4,414,128; and 4,540,505. For example, U.S. Pat. No. 4,414,128 broadly discloses an aqueous liquid detergent composition characterized by, by weight:

(a) from 1% to 20% of a synthetic anionic, nonionic, amphoteric or zwitterionic surfactant or mixture thereof;

(b) from 0.5% to 10% of a mono- or sesquiterpene or mixture thereof, at a weight ratio of (a):(b) lying in the range of 5:1 to 1:3; and (c) from 0.5% 10% of a polar solvent having a solubility in water at 15° C. in the range of from 0.2% to 10%. Other ingredients present in the formulations disclosed in this patent include from 0.05% to 2% by weight of an alkali metal, ammonium or alkanolammonium soap of a $C_{13}$–$C_{24}$ fatty acid; a calcium sequestrant from 0.5% to 13% by weight; non-aqueous solvent, e.g., alcohols and glycol ethers, up to 10% by weight; and hydrotropes, e.g., urea, ethanolamines, salts of lower alkylaryl sulfonates, up to 10% by weight. All of the formulations shown in the Examples of this patent include relatively large amounts of detergent builder salts which are detrimental to surface shine and/or leave important residue after the product has been used/sprayed.

U.S. Pat. No. 5,082,584 discloses a microemulsion composition having an anionic surfactant, a cosurfactant, nonionic surfactant, perfume and water; however, these compositions do not contain acaricidal agents.

U.S. Pat. No. 4,666,940 discloses acaricidal agents in combination with solid components that leave a residue on the surface being treated.

One well known property of microemulsions is their behaviour to solubilize high amount of oil or non water soluble components. Active ingredients like pesticides, fungicides or acaricidal agents can be easily formulated in microemulsion compositions having low amount of surfactants. Those ingredients become also chemically more stable over time and their activity has been shown higher than when solubilized in a standard o/w or w/o emulsion.

SUMMARY OF THE INVENTION

The present invention provides an improved, sprayable cleaning composition, preferably but not limited to a microemulsion form and containing d-phenothrin, piperonyl butoxide and optionally at least one supplemental acaricidal agent. The composition is suitable for the treatment of soft surfaces like mattresses and upholstery. More particularly, the improved compositions exhibit acaricidal activity, when used in undiluted (neat) form and leave the treated surfaces free of dust mites.

The instant compositions can also better solubilize the greasy natural film protection around living pests such as dust mites and can better dispense the acaricidal ingredient microsolubilized in the microemulsion, thereby being more effective in killing living dust mite killing.

Even more interesting microemulsion compositions will be those which contain also a cationic compound which is able, by its fungicidal properties, to control or to avoid the growth of Aspergillus penicilloides, Aspergillus amstelodami and Aspergillus which are known living in symbiosis with dust mites to help them to predigest their food. Reducing the amount of Aspergillus will, in addition to the acaricidal agent, drastically reduce the population of dust mites.

In one aspect, the invention generally provides a stable, sprayable, soft surface treatment composition which comprises approximately on a weight basis:

1% to 10% of at least one surfactant selected from the group consisting of nonionic, and cationic surfactants and mixtures thereof;

0 to 15% of a water-mixable cosurfactant having either limited ability or substantially no ability to dissolve oily or greasy soil;

0 to 5%, more preferably 0.1% to 5% of a water insoluble hydrocarbon, essential oil or perfume;

0 to 3%, more preferably 0.1% to 2% of piperonyl butoxide;

0.025% to 1.5% of d-phenothrin;

0 to 5.0% of at least one supplemental acaricidal agent; and the balance being water, wherein the composition does not contain a solid component having a mean particle size of 2 to 100 microns which would leave a pulverulent residue on the surface being treated or quartz, sand, siliceous earth, metal carbonate, $SiO_2$, amorphous silica, silicates, polyacrylates or xanthan gum. Explicitly excluded from the instant compositions are anionic surfactants containing a sulfate, sulfonate or a carboxylate groups, alkanol amines, amines, phenol and phenolic compounds which do not have an ester group and N-lower alkyl neoalkanolamides such as methyl neodecamide and N,N-diethyl-meta-toluamide.

DETAILED DESCRIPTION OF THE INVENTION

The present invention relates to a stable sprayable composition for the treatment of soft surfaces comprising approximately by weight: 0.1% to 10% of at least one surfactant selected from the group consisting of nonionic and cationic surfactants and mixtures thereof, 0 to 3%, more preferably 0.1% to 2% of piperonyl butoxide; 0.025% to 1.5% of d-phenothrin; 0 to 5.0% of at least one supplemental acaricidal agent, 0 to 15% of a cosurfactant or 1 to 5% of a solubilizer such as a $C_2$–$C_3$ alkanol, 0 to 5%, more preferably 0.1% to 5% of a water insoluble hydrocarbon, essential oil or perfume and the balance being water, wherein the composition does not contain a solid component having a mean particle size of 2 to 100 microns which would leave a pulverulent residue on the surface being treated or quartz, sand, siliceous earth, metal carbonate, $SiO_2$, amorphous silica, silicates, polyacrylates, xanthan gum. Explicitly excluded from the instant compositions are anionic surfactants containing a sulfate, sulfonate or carboxylate groups, alkanol amines, amines, phenol and phenolic compounds which do not have an ester group and N-lower alkyl neoalkanolamides such as methyl neodecamide and N,N-diethyl-meta-toluamide.

According to the present invention, the role of the hydrocarbon can be provided by a non-water-soluble perfume. Typically, in aqueous based compositions the presence of a solubilizers, such as alkali metal lower alkyl aryl sulfonate hydrotrope, triethanolamine, urea, etc., is required for perfume dissolution, especially at perfume levels of 0.1% and higher, since perfumes are generally a mixture of fragrant essential oils and aromatic compounds which are generally not water-soluble. Therefore, by incorporating the perfume into the aqueous cleaning composition as the oil (hydrocarbon) phase of the ultimate o/w microemulsion composition, several different important advantages are achieved such as an antimicrobial effect.

As used herein and in the appended claims the term "perfume" is used in its ordinary sense to refer to and include any non-water soluble fragrant substance or mixture of substances including natural (i.e., obtained by extraction of flower, herb, blossom or plant), artificial (i.e., mixture of natural oils or oil constituents) and synthetically produced substance) odoriferous substances. Typically, perfumes are complex mixtures of blends of various organic compounds such as alcohols, aldehydes, ethers, aromatic compounds and varying amounts of essential oils (e.g., terpenes) such as from 0% to 80%, usually from 10% to 70% by weight, the essential oils themselves being volatile odoriferous compounds and also serving to dissolve the other components of the perfume, wherein the solvent of the perfume which can be 50 to 70 wt. % of the perfume can exhibit acaricidal activity.

In the present invention the precise composition of the perfume is of no particular consequence to cleaning performance so long as it meets the criteria of water immiscibility and having a pleasing odor. Naturally, of course, especially for cleaning compositions intended for use in the home, the perfume, as well as all other ingredients, should be cosmetically acceptable, i.e., non-toxic, hypoallergenic, etc. The instant compositions show a marked improvement in ecotoxocity as compared to existing commercial products. The perfume is present in the sprayable cleaning composition in an amount of from 0.01% to 5% by weight, preferably from 0.05% to 3% by weight.

The water insoluble saturated or unsaturated organic compounds contain 4 to 20 carbon atoms and up to 4 different or identical functional groups. Examples of acceptable water insoluble saturated or unsaturated organic compound include (but are not limited to) water insoluble hydrocarbons containing 0 to 4 different or identical functional groups, water insoluble aromatic hydrocarbons containing 0 to 4 different or identical functional groups, water insoluble heterocyclic compounds containing 0 to 4 different or identical functional groups, water insoluble ethers containing 0 to 3 different or identical functional groups, water insoluble alcohols containing 0 to 3 different or identical functional groups, water insoluble amines containing 0 to 3 different or identical functional groups, water insoluble esters containing 0 to 3 different or identical functional groups, water insoluble carboxylic acids containing 0 to 3 different or identical functional groups, water insoluble amides containing 0 to 3 different or identical functional groups, water insoluble nitriles containing 0 to 3 different or dentical functional group, water insoluble akdehydes containing 0 to 3 different or dentical functional groups, water insoluble ketones containing 0 to 3 different or dentical functional groups, water insoluble phenols containing 0 to 3 different or identical functional groups, water insoluble nitro compounds containing 0 tO 3 different or identical functional groups, water insoluble halogens containing 0 to 3 different or identical functional groups, water insoluble sulfates or sulfonates containing 0 to 3 different or identical functional groups, limonene, dipentene, terpineol, essential oils, perfumes, water insoluble organic compounds containing up to 4 different or identical functional groups such as an alkyl cyclohexane having both three hydroxys and one ester group and mixture thereof.

Typical heterocyclic compounds are 2,5-dimethylhydrofuran,2-methyl-1,3-dioxolane, 2-ethyl 2-methyl 1,3 dioxolane, 3-ethyl 4-propyl tetrahydropyran, 3-morpholino-1,2-propanediol and N-isopropyl morpholine A typical amine is alphamethyl benzyldimethylamine. Typical halogens are 4-bromotoluene, butyl chloroform and methyl perchloropropane. Typical hydrocarbons are 1,3-dimethylcyclohexane, cyclohexyl-1 decane, methyl-3 cyclohexyl-9 nonane, methyl-3 cyclohexyl-6 nonane, dimethyl cycloheptane, trimethyl cyclopentane, ethyl-2 isopropyl-4 cyclohexane. Typical aromatic hydrocarbons are bromotoluene, diethyl benzene, cyclohexyl bromoxylene, ethyl-3 pentyl-4 toluene, tetrahydronaphthalene, nitrobenzene and methyl naphthalene. Typical water insoluble esters are benzyl acetate, dicyclopentadienylacetate, isononyl acetate, isobornyl acetate and isobutyl isobutyrate. Typical water insoluble ethers are di(alphamethyl benzyl) ether and diphenyl ether. Typical alcohols are phenoxyethanol and 3-morpholino-1,2-propanediol. Typical water insoluble nitro derivatives are nitro butane and nitrobenzene.

Suitable essential oils are selected from the group consisting of: Anethole 20/21 natural, Aniseed oil china star, Aniseed oil globe brand, Balsam (Peru), Basil oil (India), Black pepper oil, Black pepper oleoresin 40/20, Bois de Rose (Brazil) FOB, Borneol Flakes (China), Camphor oil, White, Camphor powder synthetic technical, Cananga oil (Java), Cardamom oil, Cassia oil (China), Cedarwood oil (China) BP, Cinnamon bark oil, Cinnamon leaf oil, Citronella oil, Clove bud oil, Clove leaf, Coriander (Russia), Coumarin 69° C. (China), Cyclamen Aldehyde, Diphenyl oxide, Ethyl anilin, Eucalyptol, Eucalyptus oil, Eucalyptus citriodora, Fennel oil, Geranium oil, Ginger oil, Ginger oleoresin (India), White grapefruit oil, Guaiacwood oil, Gurjun balsam, Heliotropin, Isobornyl acetate, Isolongifolene, Juniper berry oil, L-methyl acetate, Lavender oil, Lemon oil, Lemongrass oil, Lime oil distilled, Litsea Cubeba oil, Longifolene, Menthol crystals, Methyl cedryl ketone, Methyl chavicol, Methyl salicylate, Musk ambrette, Musk ketone, Musk xylol, Nutmeg oil, Orange oil, Patchouli oil, Peppermint oil, Phenyl ethyl alcohol, Pimento berry oil, Pimento leaf oil, Rosalin, Sandalwood oil, Sandenol, Sage oil, Clary sage, Sassafras oil, Spearmint oil, Spike lavender, Tagetes, Tea tree oil, Vanilin, Vetyver oil (Java), Wintergreen, Allocimene, Arbanex™, Arbanol®, Bergamot oils, Camphene, Alpha-Campholenic aldehyde, I-Carvone, Cineoles, Citral, Citronellol Terpenes, Alpha-Citronellol, Citronellyl Acetate, Citronellyl Nitrile, Para-Cymene, Dihydroanethole, Dihydrocarveol, d-Dihydrocarvone, Dihydrolinalool, Dihydromyrcene, Dihydromyrcenol, Dihydromyrcenyl Acetate, Dihydroterpineol, Dimethyloctanal, Dimethyloctanol, Dimethyloctanyl Acetate, Estragole, Ethyl-2 Methylbutyrate, Fenchol, Fernlol™, Florilys™, Geraniol, Geranyl Acetate, Geranyl Nitrile, Glidmint™ Mint oils, Glidox™, Grapefruit oils, trans-2-Hexenal, trans-2-Hexenol, cis-3-Hexenyl Isovalerate, cis-3-Hexanyl-2-methylbutyrate, Hexyl Isovalerate, Hexyl-2-methylbutyrate, Hydroxycitronellal, Ionone, Isobornyl Methylether, Linalool, Linalool Oxide, Linalyl Acetate, Menthane Hydroperoxide, I-Methyl Acetate, Methyl Hexyl Ether, Methyl-2-methylbutyrate, 2-Methylbutyl Isovalerate, Myrcene, Nerol, Neryl Acetate, 3-Octanol, 3-Octyl Acetate, Phenyl Ethyl-2-methylbutyrate, Petitgrain oil, cis-Pinane, Pinane Hydroperoxide, Pinanol, Pine Ester, Pine Needle oils, Pine oil, alpha-Pinene, beta-Pinene, alpha-Pinene Oxide, Plinol, Plinyl Acetate, Pseudo Ionone, Rhodinol, Rhodinyl Acetate, Spice oils, alpha-Terpinene, gamma-Terpinene, Terpinene-4-OL, Terpineol, Terpinolene, Terpinyl Acetate, Tetrahydrolinalool, Tetrahydrolinalyl Acetate, Tetrahydromyrcenol, Tetralol®, Tomato oils, Vitalizair, Zestoral™. Fifty to 70 wt. % of the perfume or essential oil may exhibit acaricidal activity.

The water-soluble organic surfactant materials which are used in forming the sprayable cleaning compositions of this invention may be selected from the group consisting of nonionic surfactants and cationic surfactants and mixtures thereof.

The water soluble nonionic surfactants which can be utilized in this invention are commercially well known and include the primary aliphatic alcohol ethoxylates, secondary aliphatic alcohol ethoxylates, alkylphenol ethoxylates and ethylene-oxide-propylene oxide condensates on primary alkanols, such a Plurafacs (BASF) and condensates of ethylene oxide with sorbitan fatty acid esters such as the Tweens (ICI). The nonionic synthetic organic surfactants generally are the condensation products of an organic aliphatic or alkyl aromatic hydrophobic compound and hydrophilic ethylene oxide groups or ethylene oxide and propylene oxide. Practically any hydrophobic compound having a carboxy, hydroxy, amido, or amino group with a free hydrogen attached to the nitrogen can be condensed with ethylene oxide or with the polyhydration product thereof, polyethylene glycol, to form a water-soluble nonionic detergent. Further, the length of the polyethenoxy chain can be adjusted to achieve the desired balance between the hydrophobic and hydrophilic elements.

The nonionic surfactants class includes the condensation products of a higher alcohol (e.g., an alkanol containing about 8 to 18 carbon atoms in a straight or branched chain configuration) condensed with about 5 to 30 moles of ethylene oxide, for example, lauryl or myristyl alcohol condensed with about 16 moles of ethylene oxide (EO), tridecanol condensed with about 6 to moles of EO, myristyl alcohol condensed with about 10 moles of EO per mole of myristyl alcohol, the condensation product of EO with a cut of coconut fatty alcohol containing a mixture of fatty alcohols with alkyl chains varying from 10 to about 14 carbon atoms in length and wherein the condensate contains either about 6 moles of EO per mole of total alcohol or about 9 moles of EO per mole of alcohol and tallow alcohol ethoxylates containing 6 EO to 11 EO per mole of alcohol.

A preferred group of the foregoing nonionic surfactants are the Neodol ethoxylates (Shell Co.), which are higher aliphatic, primary alcohol containing about 9–15 carbon atoms, such as $C_9$–$C_{11}$ alkanol condensed with 8 moles of ethylene oxide (Neodol 91-8), $C_{12-13}$ alkanol condensed with 6.5 moles ethylene oxide (Neodol 23-6.5), $C_{12-15}$ alkanol condensed with 12 moles ethylene oxide (Neodol 25-12), $C_{14-15}$ alkanol condensed with 13 moles ethylene oxide (Neodol 45-13), and the like. Such ethoxamers have an HLB (hydrophobic lipophilic balance) value of about 8–15 and give good O/W emulsification, whereas ethoxamers with HLB values below 8 contain less than 5 ethyleneoxide groups and tend to be poor emulsifiers and poor detergents.

Additional satisfactory water soluble alcohol ethylene oxide condensates are the condensation products of a secondary aliphatic alcohol containing 8 to 18 carbon atoms in a straight or branched chain configuration condensed with 5 to 30 moles of ethylene oxide. Examples of commercially available nonionic detergents of the foregoing type are $C_{11}$–$C_{15}$ secondary alkanol condensed with either 9 EO (Tergitol 15-S-9) or 12 EO (Tergitol 15-S-12) marketed by Union Carbide.

Other suitable water-soluble nonionic detergents which are less preferred are marketed under the trade name "Pluronics". The compounds are formed by condensing ethylene oxide with a hydrophobic base formed by the condensation of propylene oxide with propylene glycol. The molecular weight of the hydrophobic portion of the molecule is of the order of 950 to 4000 and preferably 200 to 2,500. The addition of polyoxyethylene radicals to the hydrophobic portion tends to increase the solubility of the molecule as a whole so as to make the surfactant water-soluble. The molecular weight of the block polymers varies from 1,000 to 15,000 and the polyethylene oxide content may comprise 20% to 80% by weight. Preferably, these surfactants will be in liquid form and satisfactory surfactants are available as grades L 62 and L 64.

The water soluble nonionic surfactants which can be utilized in this invention are an aliphatic ethoxylated/propoxylated nonionic surfactants which are depicted by the formula:

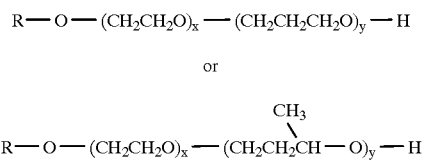

or $$R-O-(CH_2CH_2O)_x-(CH_2CH_2CH-O)_y-H$$
with CH$_3$ branch wherein R is a branched chain alkyl group having about 10 to about 16 carbon atoms, preferably an isotridecyl group and x and y are independently numbered from 1 to 20. A preferred ethoxylated/propoxylated nonionic surfactant is Plurafac® 300 manufactured by BASF.

Other suitable nonionic surfactants include the polyethylene oxide condensates of one mole of alkyl phenol containing from about 8 to 18 carbon atoms in a straight- or branched chain alkyl group with about 5 to 30 moles of ethylene oxide. Specific examples of alkyl phenol ethoxylates include nonyl phenol condensed with about 9.5 moles of EO per mole of nonyl phenol, dinonyl phenol condensed with about 12 moles of EO per mole of dinonyl phenol, dinonyl phenol condensed with about 15 moles of EO per mole of phenol and di-isoctylphenol condensed with about 15 moles of EO per mole of phenol. Commercially available nonionic surfactants of this type include Igepal CO-630 (nonyl phenol ethoxylate) marketed by GAF Corporation.

Condensates of 2 to 30 moles of ethylene oxide with sorbitan mono- and tri-$C_{10}$–$C_{20}$ alkanoic acid esters having a HLB of 8 to 15 also may be employed as the nonionic detergent ingredient. These surfactants are well known and are available from Imperial Chemical Industries under the Tween trade name. Suitable surfactants include polyoxyethylene (4) sorbitan monolaurate, polyoxyethylene (4) sorbitan monostearate, polyoxyethylene (20) sorbitan trioleate and polyoxyethylene (20) sorbitan tristearate.

The concentration of the nonionic surfactant in the composition is about 0 to 10 wt. %, more preferably 1 wt. % to 6 wt. %.

The water soluble cationic surfactants which can be utilized in this invention are iso alkyl quatarnary ammonium halides such as a decyl isononyl dimethyl ammonium chloride (Bardac 2170 ex Lonza) and benzyl dimethyl ammonium chloride (Protectol D50 ex Basf). The concentration of the cationic surfactant is 0 to about 3 wt. %, more preferably 0.1 wt. % to 2 wt. %.

Highly suitable cosurfactants used in the instant composition are water-soluble N-alkyl pyrrolidone, wherein the alkyl group has 8 to 12 carbon atoms such as N-octyl pyrrolidone, $C_3$–$C_4$ alkanols, polypropylene glycol of the formula HO(CH$_3$CHCH$_2$O)$_n$H wherein n is a number from 2 to 18 and monoalkyl ethers and esters of ethylene glycol and propylene glycol having the structural formulas R(X)$_n$OH and R$_1$(X)$_n$OH wherein R is $C_1$–$C_6$ alkyl, R$_1$ is $C_2$–$C_4$ acyl group, X is (OCH$_2$CH$_2$) or (OCH$_2$(CH$_3$)CH) and n is a number from 1 to 4.

Representative members of the polypropylene glycol include dipropylene glycol and polypropylene glycol having a molecular weight of 200 to 1000, e.g., polypropylene glycol 400. Satisfactory glycol ethers and esters are ethylene glycol monobutyl ether (butyl cellosolve), diethylene glycol monobutyl ether (butyl carbitol), triethylene glycol monobutyl ether, mono, di, tri propylene glycol monobutyl ether, tetraethylene glycol monobutyl ether, propylene glycol tertiary butyl ether, ethylene glycol monoacetate and dipropylene glycol propionate. When these glycol type cosurfactants are at a concentration of at least 1.0 weight %, more preferably at least 2.0 weight % in combination with a perfume at a concentration of at least 0.5 weight %, more preferably 1.5 weight % one can form a liquid crystal composition.

The amount of cosurfactant required to stabilize the liquid crystal compositions or the microemulsion compositions will, of course, depend on such factors as the surface tension characteristics of the cosurfactant, the type and amounts of the primary surfactants and perfumes, and the type and amounts of any other additional ingredients which may be present in the composition and which have an influence on the thermodynamic factors enumerated above. Generally, amounts of cosurfactant in the range of from 0% to 15%, preferably from 0.5% to 10%, by weight provide stable dilute o/w microemulsions for the above-described levels of primary surfactants and perfume and any other additional ingredients as described below.

The instant composition can also optionally contain 0 to 10%, more preferably 0.1 to 8%, by weight of a zwitterionic surfactant. The zwitterionic surfactant is a water-soluble betaine having the general formula:

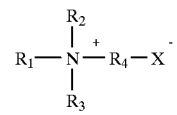

wherein $X^-$ is selected from the group consisting of $CO_2$— and $SO_3$— and R$_1$ is an alkyl group having 10 to about 20 carbon atoms, preferably 12 to 16 carbon atoms, or the amido radical:

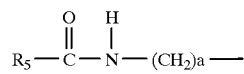

wherein R$_5$ is an alkyl group having about 9 to 19 carbon atoms and a is the integer 1 to 4; R$_2$ and R$_3$ are each alkyl groups having 1 to 3 carbons and preferably 1 carbon; R$_4$ is an alkylene or hydroxyalkylene group having from 1 to 4 carbon atoms and, optionally, one hydroxyl group. Typical alkyldimethyl betaines include decyl dimethyl betaine or 2-(N-decyl-N, N-dimethyl-ammonia) acetate, coco dimethyl betaine or 2-(N-coco N, N-dimethylammonia) acetate, myristyl dimethyl betaine, plamityl dimethyl betaine, lauryl dimethyl betaine, cetyl dimethyl betaine, stearyl dimethyl betaine, etc. The amidobetaines similarly include cocoamidoethylbetaine, cocoamidopropyl betaine and the like. A preferred betaine is coco ($C_8$-$C_{18}$) amidopropyl dimethyl betaine. Two preferred betaine surfactants are Rewoteric AMB 13 and Golmschmidt Betaine L7.

The amine oxides which can be optionally used in the instant formula are depicted by:

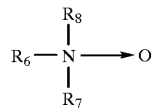

wherein $R_6$ is a $C_{10}$-$C_{18}$ linear or branched chain alkyl group, $R_7$ is a $C_1$-$C_{16}$ linear alkyl group and $R_8$ is a $C_1$-$C_{16}$ linear alkyl group.

Solubilizing agents useful in the instant compositions are $C_1$-$C_3$ mono and di-hydroxy alkanols, e.g., methanol, ethanol, isopropanol and propylene glycol. Suitable water soluble hydrotropic salts include sodium, potassium, ammonium and mono-, di- and triethanolammonium salts of benzene or cumene sulfonate. While the aqueous medium is primarily water, preferably said solubilizing agents are included in order to control the viscosity of the liquid composition and to control low temperature cloud clear properties. Usually, it is desirable to maintain clarity to a temperature in the range of 5° C. to 10° C. Therefore, the proportion of solubilizer generally will be from about 1% to 50%, preferably 1% to 40% by weight of the composition. Preferably the solubilizing ingredient will be a mixture of ethanol and a water soluble salt of a $C_1$-$C_3$ substituted benzene sulfonate hydrotrope such as sodium xylene sulfonate or sodium cumene sulfonate or a mixture of said sulfonates or ethanol and urea. Another solubilizing agent used at a concentration of about 1 to 10 wt. % is octyl pyrrolidone. Inorganic alkali metal or alkaline earth metal salts such as sodium sulfate, magnesium sulfate, sodium chloride and sodium citrate can be added at concentrations of 0.5 to 4.0 wt. % to modify the cloud point of the nonionic surfactant and thereby control the haze of the resultant solution. Various other ingredients such as urea at a concentration of about 0.5 to 4.0 wt. % or urea at the same concentration in combination with ethanol at a concentration of about 0.5 to 4.0 wt. % can be used as solubilizing agents. Other ingredients which have been added to the compositions at concentrations of about 0.1 to 4.0 wt. percent are perfumes, preservatives, such as methyl parabem (p-hydroxy benzoate) color stabilizers, sodium bisulfite, ETDA, citric acid and proteins such as lexine protein. One to 4 wt. % of an alkali metal salt of isethionic acid having the formula $CH_2OHCHSO_3H$ can be used in the amide free formula of the instant composition as a substitute for the amide as a solubilizing agent.

In addition to the previously mentioned essential and optional constituents of the cleaning composition, one may also employ normal and conventional adjuvants, provided they do not adversely affect the properties of the composition. Thus, there may be used various coloring agents and perfumes; sequestering agents such as ethylene diamine tetraacetates; magnesium sulfate heptahydrate; pearlescing agents and opacifiers; pH modifiers; etc. The proportion of such adjuvant materials, in total will normally not exceed 15% of weight of the detergent composition, and the percentages of most of such individual components will be about 0.1 to 5% by weight and preferably less than about 2% by weight. Sodium bisulfite can be used as a color stabilizer at a concentration of about 0.01 to 0.2 wt. %. Typical perservatives are dibromodicyano-butane, citric acid, benzylic alcohol and poly (hexamethylene-biguamide) hydrochloride and mixtures thereof.

The composition contains 0 to 3% by weight, more preferably 0.1 to 2% by weight of piperonyl butoxide which exhibits acaricidal activity. The composition also contains 0.025% to 1.5% by weight, more preferably 0.04% to 1.0% by weight of d-phenothrin which also exhibits acaricidal activity.

The supplemental acaricidal agent which can be used in the sprayable cleaning composition, at a concentration of about 0 to 5.0 wt. %, more preferably 0.05 to 3 wt. % is selected from the group consisting of

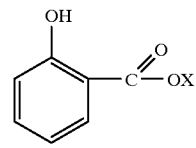

wherein

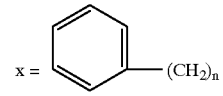

or a $C_6$-$C_{14}$ alkyl group, wherein n equals 0 to 3;

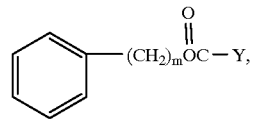

wherein m=1 to 3 and x is a $C_1$ to $C_6$ alkyl group,

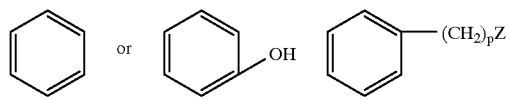

wherein p=1 to 3 and Z is a

group; carvone; citral limarome; 50 wt. thymol in benzyl benzoate; alpha pinene;citronellol dextro;hedione; linalool citronella; eucalyptus globulux; thyme white; lavandin oil grosso; a $C_6$ to $C_{14}$ aldehyde such as methyl nonyl aldehyde, hexylcinnamic aldehyde; litsea cubebaoil; 50 wt. % camphor white in benzyl benzoate; terpenolene; rosemary oil. terpineol and verdox; 50 wt. % of menthol in benzyl benzoate. Especially preferred supplemental acaricidal agents phenyl salicylate are methyl-parahydroxy benzoate, benzyl benzoate, benzyl alcohol, benzyl salicylate, benzophenone, acetophenone, benzyl acetate, isobutyl benzoate, phenyl ethyl acetate or benzoate, benzaldehyde, carvone, methyl salicylate, citral lemarome, 50 wt. % of thymol in benzyl benzoate, 50 wt. % of camphor white in benzyl benzoate and 50 wt. % of menthol in benzyl benzoate and mixtures thereof.

Examples of the cationic germicides useful in the practice of the present invention at a concentration of 0 to 10 wt. %, more preferably 0.1 to 5 wt. % include cationic surfactant-type germicides such as benzethonium chloride, benzalkonium chloride, dialkyldimethylammonium halides, monoalkyltrimethylammonium halides and their variants having the counter ions thereof changed to other anions; biguanide type germicides such as chlorhexidine and chlorhexidine gluconate; amino acid surfactants such as alkyidiamino ethylglycines and alkylpolyamino ethylglycines; and the like. The cationic germicides carry a positive charge and are typically ion-paired with a counter anion so as to provide a neutral salt when in the solid phase. Other useful cationic germicides are described in the *The Merck Index*, Merck & Co., Inc., Rahway, N.J. 1989 incorporated herein by reference. Mixtures of cationic germicides can be used.

The cationic surfactant which can be used in the present invention at a concentration of 0 to 10 wt. %, more preferably 0.1 to 5 wt. % can be any cationic surfactant with a sanitizing action well known in the art. Examples of such cationic detergent surfactants are the quaternary ammonium compounds, such as the mono- or di(long chain alkyl) tri- or di(short chain) alkyl quaternary ammonium salts; mono- or di(long chain alkyl) imidazolinium compounds; substituted long chain alkyl polyamine salts; alkyl pyridinium salts and so on. Further suitable examples can be found in Schwartz, Perry and Berch, Vol. II (1958), "Surface-active Agents and Detergents" under the heading "Cationic Surface Active Agents". The water soluble cationic surfactants which can be utilized in this invention are iso alkyl quaternary ammonium halides such as a decyl isononyl dimethyl ammonium chloride (Bardac 2170 ex Lonza) and benzyl dimethyl ammonium chloride (Protectol D50 ex BASF).

The final essential ingredient in the inventive sprayable cleaning compositions is water.

The sprayable cleaning composition, of this invention may, if desired, also contain other components either to provide additional effect or to make the product more attractive to the consumer. The following are mentioned by way of example: Colors or dyes in amounts up to 0.5% by weight; bactericides in amounts up to 1% by weight; preservatives or antioxidizing agents, such as formalin, 5-bromo-5-nitro-dioxan-1,3; 5-chloro-2-methyl-4-isothaliazolin-3-one, 2,6-di-tert.butyl-p-cresol, etc., in amounts up to 2% by weight; and pH adjusting agents, such as sulfuric acid or sodium hydroxide, as needed as well as benzalkonium chloride at a concentration of 0.5 to 2.0 wt. %. Furthermore, if opaque compositions are desired, up to 4% by weight of an opacifier may be added.

The following examples illustrate liquid cleaning compositions of the described invention. Unless otherwise specified, all percentages are by weight. The exemplified compositions are illustrative only and do not limit the scope of the invention. Unless otherwise specified, the proportions in the examples and elsewhere in the specification are by weight.

EXAMPLE 1

The following compositions in wt. % were prepared at 25° C. by simple mixing:

|  | A | B | C |
|---|---|---|---|
| $C_{9-11}$ alcohol EO5:1 | 4.5 |  |  |
| $C_{9-11}$ alcohol EO7.5–8:1 |  | 2.5 | 2.5 |
| $C_{9-11}$ alcohol EO2.5:1 |  | 2.5 | 2.5 |
| Phenyl salicylate |  |  | 0.5 |
| d-phenothrin | 0.09 | 0.1 | 0.1 |
| Piperonyl butoxide | 0.36 | 0.4 | 0.4 |
| Diethylene glycol monobutyl ether | 5.5 |  |  |
| Propylene glycol n-butyl ether |  | 2.5 | 2.5 |
| Perfume | 0.1 | 0.1 | 0.1 |
| Benzalkonium chloride |  | 1.0 |  |
| Water | Bal. | Bal. |  |
| Contact time minutes neat product | 15 30 | 15 30 |  |
| % dead mites | 53 93 | 98 100 |  |

The acaricidal test for mites is done in liquid medium in 24 wells plastic plates. About 30 living mites are placed in the well with the nourishing culture medium and then covered with either water (background values) or the neat sprayable composition (or any other liquid product to be tested) in water and left in contact for various contact times. The remaining living mites are counted by observation under the microscope after the envisaged contact time. Contact times with mites can be 5 minutes up to 3 hours.

When the sprayable composition has been found acaricidal in the direct test, the test is repeated on carpet pieces, simulating soft surfaces such as mattresses. Carpet pieces are infested with a known amount (80–100) of dust mites and let to settle for 1 hour. Carpet pieces are then treated with the sprayable composition and the remaining living mites are counted by visual observation after 3 hours, 24 hours and 96 hours. The examination can be extended up to 7 days after the treatment.

EXAMPLE 2

The following compositions in wt. % were prepared:

|  | A | B | C |
|---|---|---|---|
| Benzalkonium chloride 50% | 0.5 | 0.5 |  |
| Cocoamidopropyl betaine 30% |  |  | 4.5 |
| LF300 | 5 |  |  |
| Dobanol 23–65 |  | 3.5 | 3.5 |
| d-phenothrin | 0.1 | 0.1 | 0.1 |
| Piperonyl butoxide | 0.4 | 0.4 | 0.4 |
| Perfume | 0.1 | 0.1 | 0.1 |
| Water | Bal. | Bal. | Bal. |

What is claimed is:

1. A sprayable composition for the treatment of soft surfaces which comprises approximately by weight:

(a) 1% to 10% of at least one surfactant selected from the group consisting of ethoxylated nonionic surfactants, ethoxylated/propoxylated nonionic surfactants, and, cationic surfactants, and mixtures thereof;

(b) 0.1% to 2% of piperonyl butoxide;

(c) 0.025% to 1.5% of d-phenothrin;

(d) 0 to 5% of at least one supplemental acaricidal agent, wherein said at least one supplemental acaricidal agent is selected from the group consisting of benzyl alcohol, phenyl salicylate, benzyl salicylate, benzyl benzoate and methyl para-hydroxy benzoate and mixtures thereof;

(e) 0.5% to 10% of a glycol ether cosurfactant selected from the group consisting of ethylene glycol monobutyl ether, diethylene glycol monobutyl ether, triethylene glycol monobutyl ether, tetraethylene glycol monobutyl ether, monopropylene glycol monobutyl ether, dipropylene glycol monobutyl ether, tripropylene glycol monobutyl ether and propylene glycol tertiary butyl ether;

(f) 0.1% to 5% of a water insoluble hydrocarbon, essential oil or perfume; and (g) the balance being water, wherein the composition does not contain a solid component having a mean particle size of 2 to 100 microns which would leave a pulverulent residue on the surface being treated or quartz, sand, siliceous earth, metal carbonate, $SiO_2$, amorphous silica, silicates, polyacrylates or xanthan gum.

2. The composition according to claim 1 wherein said surfactant is at least one ethoxylated nonionic surfactant.

3. The composition according to claim 1 wherein said surfactant is a mixture of a cationic surfactant and an ethoxylated nonionic surfactant.

* * * * *